United States Patent
Perren et al.

(10) Patent No.: US 6,827,721 B2
(45) Date of Patent: Dec. 7, 2004

(54) METHOD AND DEVICE FOR THE DETERMINATION OF REDUCTION PARAMETERS FOR THE SUBSEQUENT REDUCTION OF A FRACTURED BONE

(75) Inventors: Stephan Perren, Davos Dorf (CH); Milorad Mitkovic, Nis (YU); Markus Hehli, Frauenkirch (CH)

(73) Assignee: Synthes (USA), Paoli, PA (US)

( * ) Notice: Subject to any disclaimer, the term of this patent is extended or adjusted under 35 U.S.C. 154(b) by 139 days.

(21) Appl. No.: 10/144,849

(22) Filed: May 15, 2002

(65) Prior Publication Data

US 2003/0004518 A1 Jan. 2, 2003

Related U.S. Application Data

(63) Continuation of application No. PCT/CH99/00538, filed on Nov. 15, 1999.

(51) Int. Cl.$^7$ .............................................. A61B 17/64
(52) U.S. Cl. ..................................................... 606/102
(58) Field of Search .......................... 606/102, 54, 55, 606/56, 57, 58, 59

(56) References Cited

U.S. PATENT DOCUMENTS 4,920,959 A    5/1990  Witzel et al. ................. 606/53
5,443,464 A    8/1995  Russell et al. ................ 606/54
5,776,136 A    7/1998  Sahay et al. .................. 606/79
5,827,283 A   10/1998  Groiso et al. ................. 606/57

FOREIGN PATENT DOCUMENTS

EP    0 950 379 A    10/1999

*Primary Examiner*—Cary E. O'Connor
*Assistant Examiner*—Candice C. Melson
(74) *Attorney, Agent, or Firm*—Jones Day

(57) ABSTRACT

The invention is related to a method for the determination of reduction parameters for the subsequent adjustment of a reduction device to reduce the fragments of a fractured bonee. The method comprises: measuring points on the surfaces of the corresponding bones of interest at the patient's left and right side of the body; establishing a plane of symmetry containing an anterior-posterior axis and a proximal-distal axis; generating a mirror image of the patient's non-fractured bone symmetrically to the plane of symmetry; and determining the reduction parameters by comparison of the coordinates of the points at the fractured bone with the coordinates of the points within the mirror image. The device according to the invention comprises: a cylindric or prismatic reference bar; clamps displaceable on and fastenable to the reference bar; screws or pins screwable into the bone transversely to the reference bar within the clamps; and an adjustable clamp to fasten a pin capable of being set with its tip to desired points on the surface of the bone.

21 Claims, 4 Drawing Sheets

METHOD AND DEVICE FOR THE DETERMINATION OF REDUCTION PARAMETERS FOR THE SUBSEQUENT REDUCTION OF A FRACTURED BONE

CROSS-REFERENCE TO RELATED APPLICATIONS

This application is a continuation of the U.S. national stage designation of copending International Patent Application PCT/CH99/00538, filed Nov. 15, 1999, the entire content of which is expressly incorporated herein by reference thereto.

FIELD OF THE INVENTION

The present invention relates generally to a method for the determination of reduction parameters for the subsequent adjustment of a reduction device in order to reduce the fragments of a fractured bone.

BACKGROUND OF THE INVENTION

In the field of osteosynthesis, bone fragments of a patient's fractured bone must often be correctly relocated. Only after such a correct relocation (reduction) of the bone fragments may a fixing device, such as an external or internal fixation, be applied in order to fix the bone fragments in a rigid position. In other applications, wherein the patient has a bone malformation for example, the bone or bones must be treated.

At present, the dislocation of fragments of fractured bones must be determined by means of X-ray imaging. When using or installing an external fixation, the corrections to be made through adjustment of the respective clamps and pins or screws is based upon on these X-ray images. The verification of the reduction of the fractured bone by means of the external fixation must be effected with subsequent X-ray imaging. This procedure may be cumbersome, especially in case of multiple steps of adjustment of the fragments.

In this regard, remedial measures are desired. A need exists for a method and a device based upon the comparison of the bone contour of the fractured bone with the corresponding healthy bone on the patient's healthy side of the body without using X-ray imaging.

SUMMARY OF THE INVENTION

The invention is related to a method for the determination of reduction parameters for the subsequent adjustment of a reduction device to reduce the fragments of a fractured bone, comprising the steps of: (A) comparing the contour of a first bone on a first side of a patient's body with respect to a corresponding second bone on the opposite side of the patient's body, wherein the first bone is a non-fractured bone and the second bone is a fractured bone; (B) determining the positions of a first set of points on the first bone, and establishing a three-dimensional coordinate system with respect to the body of the patient; (C) determining the positions of a second set of on the second bone within the coordinate system, wherein the second set of points corresponds to the first set of points; (D) establishing a plane of symmetry by dividing vectors between each point of the first set and its corresponding point of the second set in two parts, and defining central points of the vectors which define the plane of symmetry within the coordinate system; (E) generating a mirror image of the first bone symmetrically to the plane of symmetry by determining the positions of a third set of points on the first bone at each section corresponding to a fragment of the second bone and by forming the mirror image of the first bone by determining the positions of a fourth set of points that are symmetrical to the third set of points with respect to the plane of symmetry; (F) determining the positions of a fifth set of points on the second bone at each fragment section, wherein the fifth set of points corresponds to the third set of points on the first bone; and (G) determining the reduction parameters by comparing the different positions of the fifth set of points on the second bone with the positions of the fourth set of points within the mirror image. In one preferred embodiment, the second set of points includes at least three points situated on a proximal fragment of the bone. In one embodiment, a plane of symmetry containing an anterior-posterior axis and a proximal-distal axis is established by means of dividing the connecting vectors between each point and its corresponding point in two equal parts therewith defining central points of the vectors which determine three points of the plane of symmetry within the coordinate system.

The coordinates are preferably measured within the coordinate system defined under step (B). The determination of the reduction parameters is then preferably executed by means of calculating the differences between the coordinates of the points at the fractured bone and the coordinates of the points within the mirror image in the medial-lateral direction, the anterior-posterior direction and the proximal-distal direction.

In another preferred embodiment of the method according to the invention, the determination of the position of the points on the surface of the fractured and the non-fractured bone is performed by means of touching these points with the tip of a pointer which is provided with at least three markers whose position is determinable within an on-site three-dimensional coordinate system by means of an optical position measurement device and respective data management via a computer.

The position measurement device may be an optical position measurement device, an acoustic position measurement device or an electromagnetic position measurement device.

Corresponding to the mode of operation of the position measurement device, the markers attached to the pointer may be energy emitting, receiving or reflecting means. For example, suitable energy emitting means that may be installed include: Light sources; light emitting diodes (LEDs); infrared light emitting diodes (IREDs); acoustic transmitters; or coils in order to establish a magnetic field. Also, suitable energy receiving means that may be installed include: photodiodes; microphones; or hall-effect components.

In another embodiment according to the invention, the method comprises: (A) the determination of the position of the at least three points at the surface of one of the bones by means of fastening one reference bar through two screws or pins to the bone and determining a third point with an adjustable pin fastenable to the reference bar; (B) the determination of the position of the identical points at the surface of the other bone by means of fastening a second reference bar through two screws or pins to the other bone and determining the third point with an adjustable pin fastenable to the reference bar; and (C) the coordinates of the tips of the adjustable pins relative to particularly defined points on the reference bars are compared in order to estimate the reduction parameters.

The method may also include: (A) the measurement of the reduction parameters relative to the medial-lateral plane by means of attaching one reference bar at the non-fractured bone in the medial-lateral plane and one reference bar at the fractured bone in the medial-lateral plane; (B) the measurement of the reduction parameters relative to the anterior-posterior plane by means of attaching one reference bar at the non-fractured bone, in the anterior-posterior plane and one reference bar at the fractured bone in the anterior-posterior plane; or (C) the measurement of the reduction parameters relative to the medial-lateral plane and relative to the anterior-posterior plane by means of attaching one reference bar each at the non-fractured bone in the medial-lateral plane and in the anterior-posterior plane and one reference bar each at the fractured bone in the medial lateral plane and in the anterior-posterior plane.

The method according to the invention is preferably performed by the surgeon as an additional step during planning and preparation of the surgical treatment of the fractured bone as for example the selection of an adequate reduction apparatus and method as well as adequate internal or external fixators.

Also disclosed is a device according to the invention comprising: a cylindric or prismatic reference bar having a longitudinal axis; clamps displaceable on the reference bar in the direction of the longitudinal axis and fastenable to the reference bar; screws or pins loosenable and fixable transversely to the reference bar within the clamps whereby the screws are screwable into the bone therewith attaching the reference bar to the bone; and one or more adjustable clamps to loosenably fasten one or more pins capable of being set with their tips to desired points on the surface of the bone.

In a preferred embodiment of the device according to the invention, the adjustable clamp is designed such that the tip of the pin is displaceable with three degrees of freedom therewith allowing to estimate the coordinates of the tip with respect to a three-dimensional coordinate system affixed to the reference bar. To realize this displaceability with three degrees of freedom the adjustable clamp comprises a socket, a post and a support whereby the support is slidable in the direction of the longitudinal axis of the post and the socket is slidable on the reference bar in the direction of the longitudinal axis of the reference bar.

Preferably the post is arranged perpendicularly to the reference bar and the support is provided with a bore hole for acceptance of the pin and with an axis extending perpendicular to the post and the reference bar.

In another embodiment of the device according to the invention, articulated pins may be provided to attach the reference bar to the bone. Preferably each articulated pin is provided with a thread at its end being introduced into the bone. At the joint of the articulated pin, a turning knuckle having one degree of freedom or a ball joint may be provided. The articulation is preferably loosenably fastenable. Advantageously, the invention preferably permits the reduction parameters of a fractured bone to be determined without the need of X-rays of the bone of interest.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
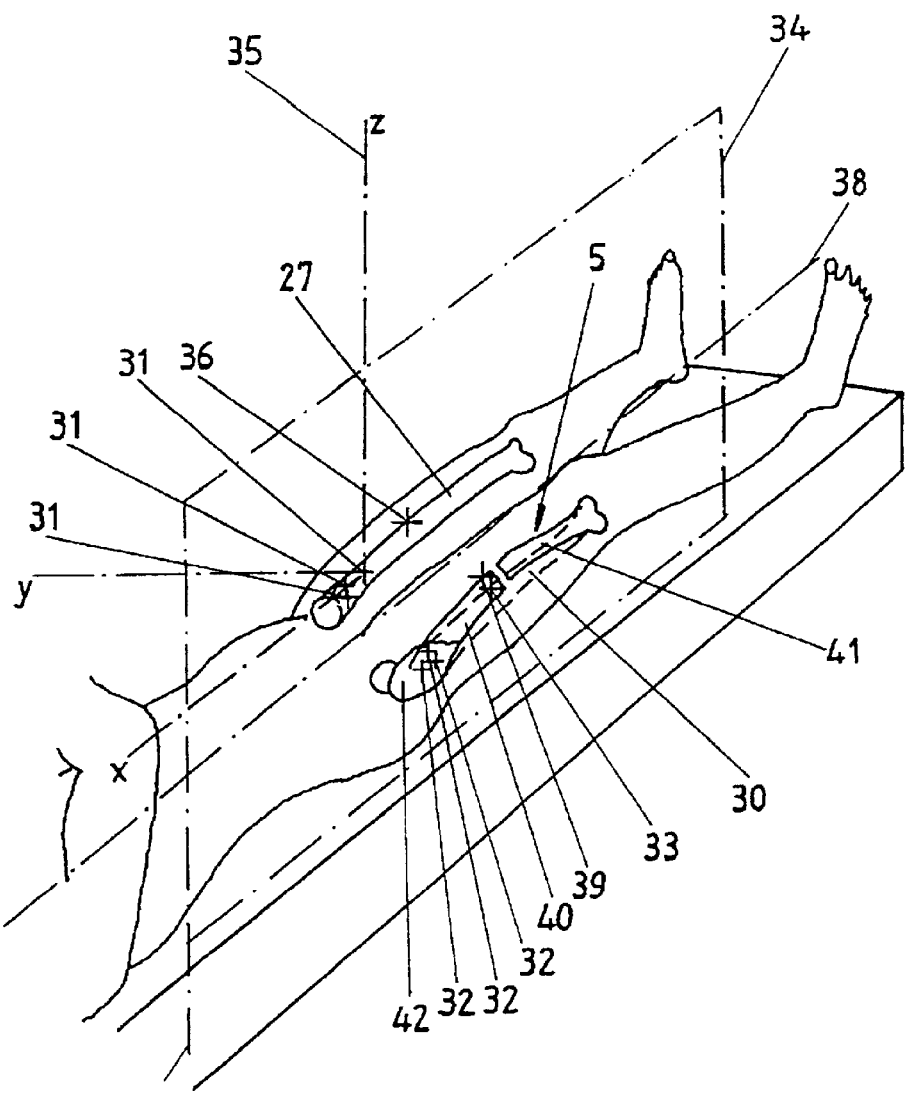
FIG. 1 shows a preferred embodiment of a method according to the invention.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

FIG. 1 illustrates a method according to the invention whereby a comparison of the bone contour of the fractured bone is made with the corresponding healthy bone on the patient's healthy side of the body. The method according to the invention is used to determine reduction or relocation parameters for the subsequent adjustment of a reduction device in order to reduce the fragments of a fractured bone 5. To obtain these reduction parameters, a preferred method according to the invention comprises the following steps:

A) the determination of the reduction parameters is performed by means of a comparison of the contour of the corresponding bones 5, 27 of interest at the patients left and right side of the body; whereby B) the positions of at least three non-collinear points 31, 32 on one of the bones 5, 27 of interest are determined, therewith establishing a three-dimensional coordinate system 35 with respect to the body of the patient;

C) the positions of the corresponding points 31, 32 on the other bone 5, 27 of interest and within the coordinate system 35 are determined. Preferably the determination of the corresponding points 32 on the fractured bone 5 is effected such that the at least three points 32 are situated on a proximal fragment 42 of the fractured bone 5;

D) a plane of symmetry 34 is established by means of dividing connecting vectors between each point 31 and its corresponding point 32 in two parts thereby defining central points of the vectors which determine three points of the plane of symmetry 34 within the coordinate system 35;

E) a mirror image 30 of the patient's non-fractured bone 27 is generated symmetrically to the plane of symmetry 34 by means of determining at least three non-collinear points 36 at the non-fractured bone 27 at each section corresponding to a fragment 40, 41, 42 of the fractured bone 5. The mirror image 30 is formed by determination of the points 33 that are symmetrical to the points 36 with respect to the plane of symmetry 34;

F) the positions of at least three points 39 at each fragment 40, 41, 42 of the fractured bone 5 and corresponding to the points 36 at the non-fractured bone 27 are determined; and G) the reduction parameters are then determined by comparison of the different positions of the points 39 at the fractured bone 5 with the positions of the points 33 within the mirror image 30.

In order to determine identical points 31, 32 on the fractured bone 5 and at the non-fractured bone 27, anatomical landmarks may be used. For instance, anatomical ridges at the great trochanter proximally and on the lateral femoral condyle distally may be used as anatomical landmarks.

Figure 2:
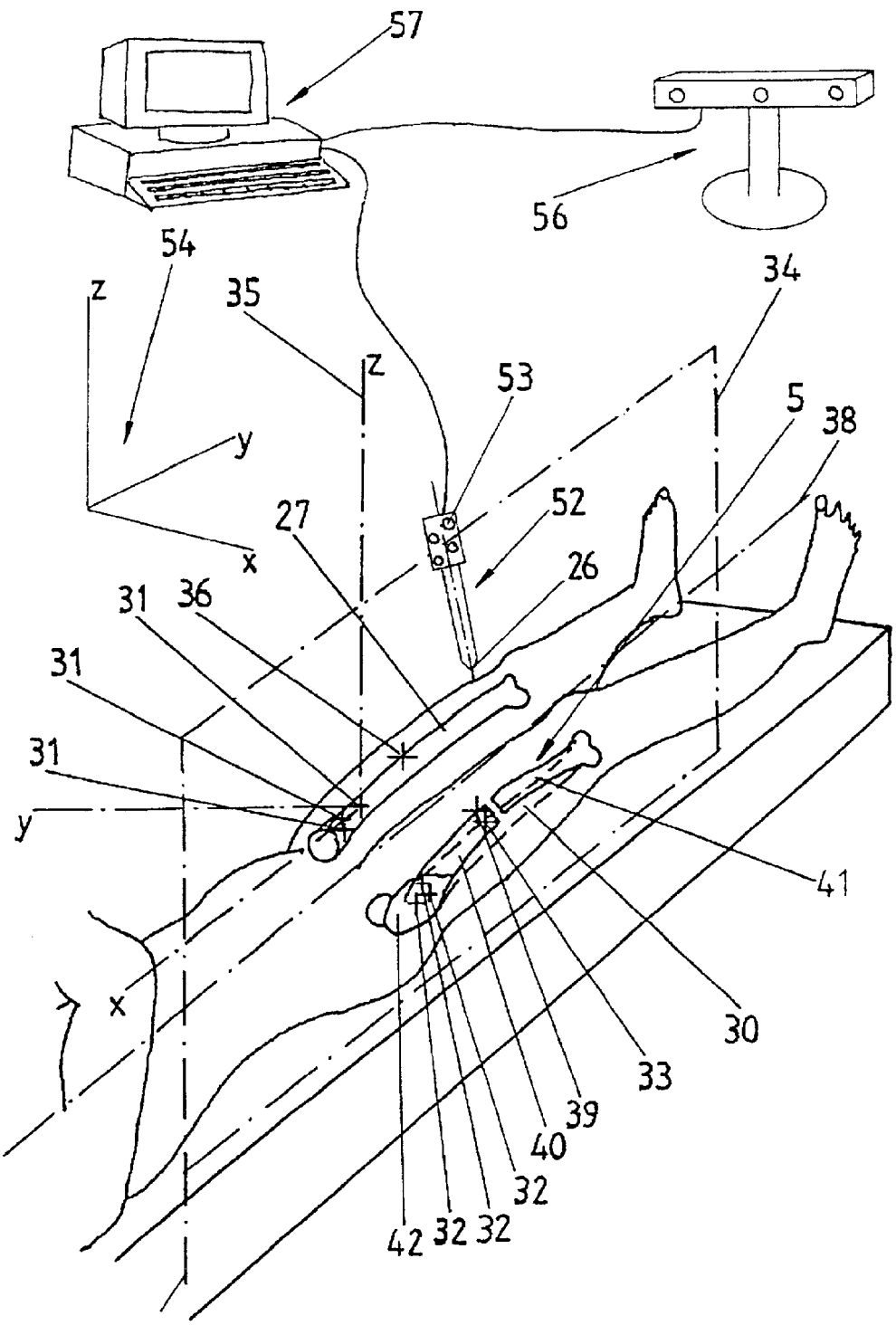
FIG. 2 shows another embodiment of the method according to the invention comprising a position measurement device and a computer.

FIG. 2 illustrates a preferred embodiment of the method according to the invention whereby the determination of the position of the at least three points 31 at one of the bones 5, 27 and the determination of the position of the identical points 32 at the other bone 5, 27 is performed by means of touching the points 31, 32 on the surface of the bones 5, 27 with the tip 26 of a pointer 52 which is provided with at least three markers 53 whose position is determinable within an on-site three-dimensional coordinate system 54 by means of an optical position measurement device 56 and respective data management via a computer 57. This realization of the method according to the invention is preferably used together with a Computer Assisted Surgery System (CAS). For instance, the position measurement device 58 may be an optoelectronic navigation system (such as Optotrak 3020, Northern Digital, CAN.). Correspondingly, the markers 53 may be infrared light emitting diodes (IRED s) that are detected by the position measurement device 56 therewith to permit the calculation of the position of the pointer tip 26 within the three-dimensional coordinate system 54.

Figure 3:
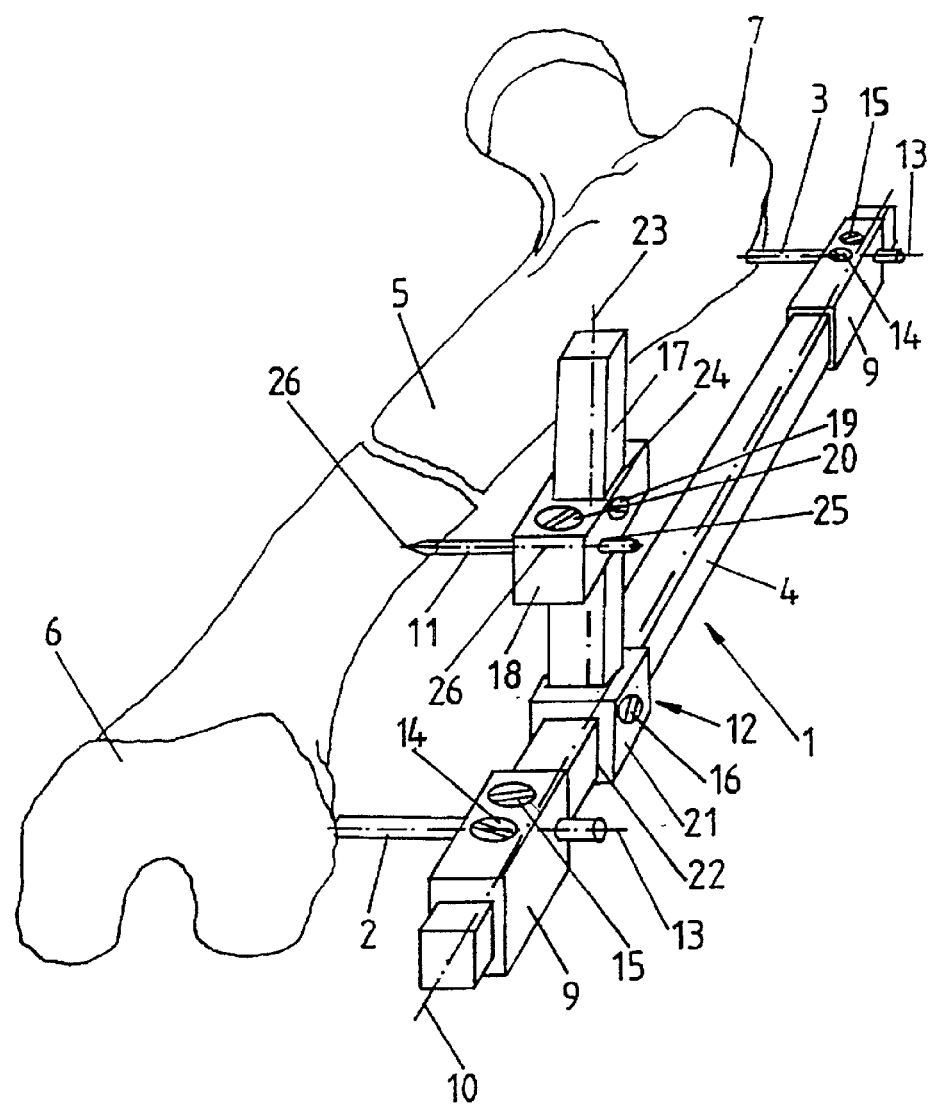
FIG. 3 shows a preferred embodiment of a device according to the invention.

FIG. 3 illustrates a preferred embodiment of a device 1 according to the invention. This device 1 may be used for the determination of reduction parameters at a fractured bone 5 and generally comprises: a prismatic reference bar 4, two clamps 9 displaceable on reference bar 4, two screws 2, 3 fixable within clamps 9, and one adjustable clamp 12 to loosenably fasten a pin 11. Reference bar 4 has a longitudinal axis 10 and preferably a square cross section. Clamps 9 are displaceable on the reference bar 4 in the direction of the longitudinal axis 10 and fastenable to the reference bar 4 by means of screws 14 that are screwed into bores containing interior threads within clamps 9 and press onto the reference bar 4 when tightened. The two screws 2, 3 or pins have axes 13 loosenable and fixable transversely to the reference bar 4 within the clamps 9 by means of screws 15 that are screwed into bores containing interior threads within clamps 9 and press onto the reference bar 4 when tightened. Screws 2,3 are screwable into the bone 5 for attaching the reference bar 4 to the bone 5. Adjustable clamp 12 loosenably fastens a pin 11 capable of being set with its tip 26 to a desired point on the surface of the bone 5.

The adjustable clamp 12 is designed such that the tip 26 of the pin 11 is displaceable with three degrees of freedom. It comprises a socket 21, a post 17 with a central axis 23 mounted rectangularly to the longitudinal axis 10 of the reference bar 4 on the socket 21 and a support 18 whereby the support 18 is slidable in the direction of the central axis 23 on the post 17 and the socket 21 is slidable on the reference bar 4 in the direction of the longitudinal axis 10. The support 18 is provided with a bore hole 25 for acceptance of the pin 11 and having an axis 26 extending perpendicular to the central axis 23 of the post 17 and perpendicular to the longitudinal axis 10 of the reference bar 4.

Figure 4:
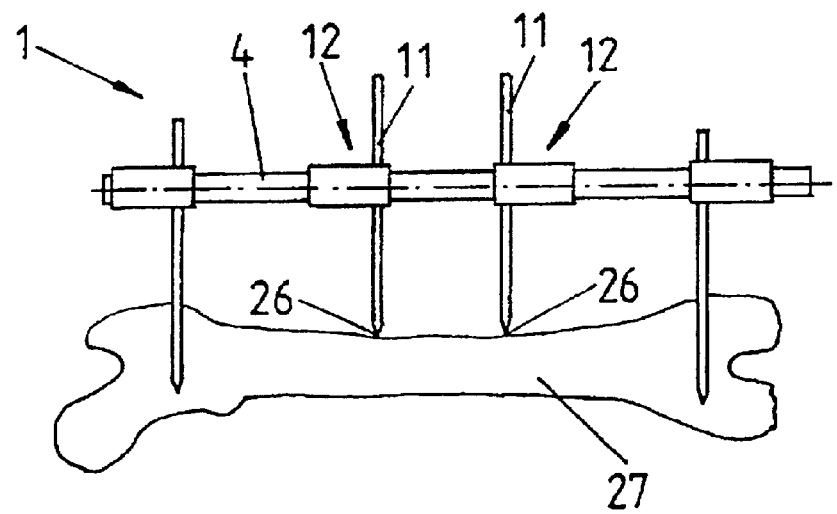
FIG. 4 shows the device of FIG. 3 attached to a non-fractured bone.
Figure 5:
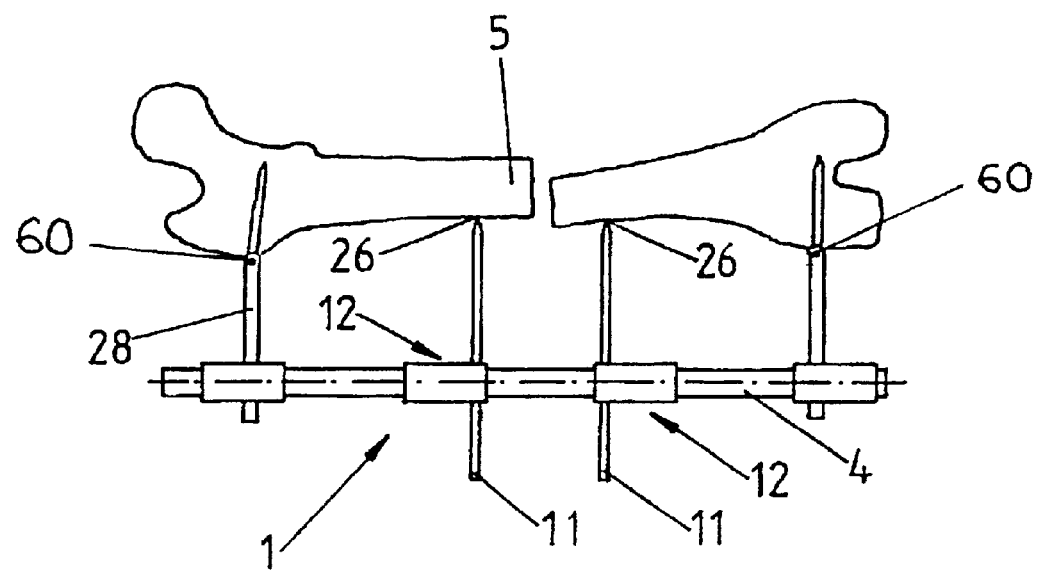
FIG. 5 shows the device of FIG. 3 attached to a fractured bone.

FIGS. 4 and 5 illustrate device 1 according to the invention mounted on a nonfractured femur 27 (FIG. 4) and mounted on a fractured femur 5 (FIG. 5). The device 1 comprises two adjustable clamps 12 each with one pin 11. Both devices 1 are attached to the bones 5, 27 in the lateral-medial plane of the patient and symmetrical to a plane defined as described in FIG. 1. The coordinates of the points of the tips 26 of the pins 11 may be measured relative to the reference bar 4 and compared. Furthermore, the device 1 shown in FIG. 5 is provided with at least one articulated pin 28.

Once the reduction parameters are determined, particularly the correction measurements of bone length and angulation of the bone fragments of the fractured bone, the correction may be performed by means of a reduction device. The correction of the position of the bone fragments preferably begins with the correction of the bone length (ordinary distraction) followed by the correction of the angulation of the bone fragments in both the horizontal and the distal planes. These corrections are performed until the same parameters, particularly the corresponding coordinates within the reference coordinate system are received. During this correction, the parameter data received from the non-fractured bone and transformed via the plane of symmetry (mirror) are used.

Finally, the clamps 21 are moved into the fracture level, one in the horizontal plane and one in the vertical plane. The tips of the pins assess the exact position of the fracture area in the horizontal and vertical planes. Particularly the assessment of any overdistraction is performed which is followed by fine corrections of small dislocations of the bone fragments. If a comminuted fracture is under procedure, the final reduction via the above pin is not performed. Subsequently, the measuring device is removed and the fixation of the bone can be performed. If an external fixation is intended to be applied, the frame of a high mobile external fixation is fixed to the end remote of the bone of these pins that were already used when performing the reduction with a reduction device. If internal fixation is performed, minimally invasive methods of osteosynthesis are recommended.

If the reduction device is computer controlled, a particular software program may be used to receive the reduction parameter data from the non-fractured bone of the patient and transform these data via the plane of symmetry (mirror) into the reduction measures and control the motors of the already attached reduction device. By means of the motors, the necessary corrections of the bone fragments is performed. Again the correction of the bone length (distraction) is performed first. Sensors at the reference bar, clamps, and pins transmit digital signals to the computer until the correction is completed. One pin can be introduced into each bone fragment and introduced in a clamp. Preferably, the pin should be mounted at a right angle to the surface of the bone to provide an easier or an automatic reduction.

The automatic reduction device is preferably provided with a control system which comprises sensors for measuring a probable over strength between the bone and reduction device connections. When this strength exceeds the allowed level the computer can switch the motors off or return the reduction device to a previous position, thereby protecting bone and soft tissues from damage. After receiving this information, the computer analyzes again the position of the bone fragments, and the motors may be controlled in order to perform more distraction or prevent collision of the bone fragments.

While various descriptions of the present invention are described above, it should be understood that the various features can be used singularly or in any combination thereof. Therefore, this invention is not to be limited to only the specifically preferred embodiments depicted herein. For instance, other suitable structures for engagement of a screw or pin may be employed. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method for the determination of reduction parameters for the subsequent adjustment of a reduction device to reduce the fragments of a fractured bone, comprising the steps of;
    (a) comparing the contour of a first bone on a first side of a patient's body with respect to a corresponding second bone on the opposite side of the patient's body, wherein the first bone is a non-fractured bone and the second bone is a fractured bone;
    (b) determining the positions of a first set of at least three non-collinear points on the first bone, and establishing a three-dimensional coordinate system with respect to the body of the patient;
    (c) determining the positions of a second set of at least three non-collinear points on the second bone within the coordinate system, wherein the second set of points corresponds to the first set of points;
    (d) establishing a plane of symmetry by dividing vectors between each point of the first set and its corresponding point of the second set in two parts, and defining central points of the vectors which define at least three points of the plane of symmetry within the coordinate system;
    (e) generating a mirror image of the first bone symmetrically to the plane of symmetry by determining the positions of a third set of at least three non-collinear points on the first bone at each section corresponding to a fragment of the second bone and by forming the mirror image of the first bone by determining the positions of a fourth set of at least three non-collinear points that are symmetrical to the third set of points with respect to the plane of symmetry;
    (f) determining the positions of a fifth set of at least three non-collinear points on the second bone at each fragment section, wherein the fifth set of points corresponds to the third set of points on the first bone; and
    (g) determining the reduction parameters by comparing the different positions of the fifth set of points on the second bone with the positions of the fourth set of points within the mirror image.

2. The method claim 1, wherein the second set of points includes at least three points situated on a proximal fragment of the bone.

3. The method claim 1, wherein determining the position of the first and second set of points is performed by means of touching the points on the surface of the bones with the tip of a pointer which is provided with at least three markers whose position is determinable within a three-dimensional coordinate system by means of an optical position measurement device and respective data management via a computer.

4. The method claim 3, wherein the first set of points and second set of points are defined by means of fiducial markers pre-operatively implanted.

5. The method claim 1, wherein the determination of the position of the first or second set of points is performed by fastening at least one reference bar to the bone through at least two screws or pins and determining a third point with an adjustable pin.

6. A device for the determination of reduction parameters of a fractured bone according to the method of claim 1, comprising:
    a cylindric or prismatic reference bar having a longitudinal axis;
    at least two clamps displaceable on the reference bar in the direction of the longitudinal axis and fastenable to the reference bar;
    at least two screws or pins with axes loosenable and fixable transversely to the reference bar within the clamps, and the screws are screwable into the bone for attaching the reference bar to the bone; and
    at least one adjustable clamp to loosenably fasten a pin tip to a desired point on the surface of the bone, wherein the adjustable clamp comprises a socket slidable on the reference bar in the direction of the longitudinal axis, a post extending from the socket and having a central axis, and a support slidable on the post in the direction of the central axis, whereby the pin tip is displaceable with three degrees of freedom.

7. The device of claim 6, wherein the central axis is arranged perpendicularly to the longitudinal axis and to the axes of the screws.

8. The device of claim 6, wherein the support defines a bore hole for accepting the pin, wherein the bore hole has an axis extending perpendicular to the central axis and perpendicular to the longitudinal axis.

9. The device of claim 6, wherein at least one pin is an articulated pin.

10. The device of claim 9, wherein the articulated pin has a threaded end to be introduced into the bone.

11. The device of claim 9, wherein the articulated pin has a turning knuckle with one degree of freedom.

12. The device of claim 11, wherein the articulated pin is provided with a ball joint.

13. The device of claim 9, wherein the articulation of the articulated pin is loosenably fastenable.

14. A device for the determination of reduction parameters of a fractured bone on one side of a patient's body based on the corresponding non-fractured bone on the opposite side of the patient's body, the device comprising:
    a first and a second reference bars attachable respectively along the fractured and the non-fractured bones;
    at least one adjustable clamp longitudinally displaceable on each reference bar to loosenaby fasten a pin tip at one or more predetermined points on the surface of each bone;
    at least one sensor coupled to each pin tip for detecting position thereof; and
    a processor configurable (i) to receive from the sensors the detected pin tip positions, (ii) to compute from the pin tip positions three-dimensional coordinates thereof, and (iii) to compare three-dimensional coordinates of the pin tips to determine reduction parameters of the fractured bone.

15. The device of claim 14, wherein the one or more predetermined points are non-collinear with respect to a reference bar.

16. The device of claim 14, wherein the adjustable clamp of each reference bar is configured such that the pin tips are displaceable with three degrees of freedom.

17. The device of claim 16, wherein each adjustable clamp comprises a socket longitudinally slidable on a reference bar, a post extending from the socket and having a central axis, and a support slidable on the post in the direction of the central axis.

18. The device of claim 14, wherein each reference bar further comprises:
    at least two clamps longitudinally displaceable on the reference bar and fastenable to the reference bar; and
    at least two screws or pins with axes loosenable and fixable transversely to the reference bar within the clamps, and the screws are screwable into a bone for attaching the reference bar to the bone.

19. The device of claim 14, wherein the first reference bar is attached to the fractured bone at a medial-lateral plane and the second reference bar is attached to the non-fractured bone at the medial-lateral plane.

20. The device of claim 14, wherein the first reference bar is attached to the fractured bone at an anterior-posterior plane and the second reference bar is attached to the non-fractured bone at the anterior-posterior plane.

21. The device of claim 14, wherein the first reference bar is attached to the fractured bone at a medial-lateral and anterior-posterior planes and the second reference bar is attached to the non-fractured bone at a medial-lateral and anterior-posterior planes.

* * * * *